United States Patent
Shah et al.

(10) Patent No.: US 9,713,476 B2
(45) Date of Patent: *Jul. 25, 2017

(54) MULTI-LAYER FILM WELDED ARTICULATED BALLOON

(71) Applicant: Polyzen Inc., Apex, NC (US)

(72) Inventors: Tilak M. Shah, Cary, NC (US); Christopher D. Strom, Cary, NC (US)

(73) Assignee: POLYZEN INC., Apex, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 13/685,448

(22) Filed: Nov. 26, 2012

(65) Prior Publication Data

US 2013/0085324 A1  Apr. 4, 2013

Related U.S. Application Data

(63) Continuation of application No. 13/154,229, filed on Jun. 6, 2011, now Pat. No. 8,740,845, which is a
(Continued)

(51) Int. Cl.
*A61B 1/32* (2006.01)
*A61B 17/12* (2006.01)
(Continued)

(52) U.S. Cl.
CPC .......... *A61B 17/12136* (2013.01); *A61B 1/32* (2013.01); *A61B 17/1285* (2013.01);
(Continued)

(58) Field of Classification Search
CPC .............. A61M 2025/1059; A61M 2025/1075
See application file for complete search history.

(56) References Cited

U.S. PATENT DOCUMENTS 2,703,770 A    3/1955  Melzer
3,164,151 A    1/1965  Nicoll
(Continued)

FOREIGN PATENT DOCUMENTS

JP    51-90376 A    8/1976
JP    51-100833 A   9/1976
(Continued)

OTHER PUBLICATIONS

Office Action Issued on Oct. 11, 2012 in U.S. Appl. No. 13/154,229 by Pritesh A. Patel.
(Continued)

*Primary Examiner* — Laura Bouchelle
*Assistant Examiner* — Anh Bui
(74) *Attorney, Agent, or Firm* — Hultquist, PLLC; Steven J. Hultquist

(57) ABSTRACT

A method of fabrication of a medical balloon, and a balloon device useful for various medical balloon procedures, such as gastrointestinal, vascular, reproductive system, urinary system and pulmonary applications. At least two layers of a thermoplastic film are sealed at their peripheral edges and heat sealed at one or more locations inside an area enclosed by the sealed edges at predetermined locations, in one implementation of the balloon device. Such configuration enables the balloon to articulate to a desired shape upon inflation, with the desired shape being selected to accommodate a specific medical application.

10 Claims, 5 Drawing Sheets

Related U.S. Application Data continuation of application No. 12/237,897, filed on Sep. 25, 2008, now Pat. No. 7,976,497.

(60) Provisional application No. 60/974,884, filed on Sep. 25, 2007.

(51) Int. Cl.

| | | |
|---|---|---|
| *A61M 25/10* | (2013.01) | |
| *B32B 37/18* | (2006.01) | |
| *A61B 17/128* | (2006.01) | |
| *A61M 39/24* | (2006.01) | |
| *B29C 65/02* | (2006.01) | |
| *B29C 65/04* | (2006.01) | |
| *B29C 65/38* | (2006.01) | |
| *B29C 65/00* | (2006.01) | |
| *B29K 101/12* | (2006.01) | |
| *B29L 9/00* | (2006.01) | |
| *B29L 22/02* | (2006.01) | |
| *B29L 31/00* | (2006.01) | |
| *B29C 65/48* | (2006.01) | |
| *A61B 17/00* | (2006.01) | |

(52) U.S. Cl.
CPC .. *A61B 17/12104* (2013.01); *A61B 17/12109* (2013.01); *A61M 25/1002* (2013.01); *A61M 25/1027* (2013.01); *A61M 39/24* (2013.01); *B29C 66/4742* (2013.01); *B32B 37/182* (2013.01); *A61B 2017/00274* (2013.01); *A61B 2017/00526* (2013.01); *A61B 2017/00778* (2013.01); *A61B 2017/00809* (2013.01); *A61B 2017/00818* (2013.01); *A61B 2017/00862* (2013.01); *A61B 2017/00955* (2013.01); *A61M 25/104* (2013.01); *A61M 2025/1075* (2013.01); *B29C 65/02* (2013.01); *B29C 65/04* (2013.01); *B29C 65/38* (2013.01); *B29C 65/48* (2013.01); *B29C 65/4895* (2013.01); *B29C 66/1122* (2013.01); *B29C 66/21* (2013.01); *B29C 66/43* (2013.01); *B29C 66/4312* (2013.01); *B29C 66/73521* (2013.01); *B29K 2101/12* (2013.01); *B29K 2995/0046* (2013.01); *B29L 2009/00* (2013.01); *B29L 2022/02* (2013.01); *B29L 2022/022* (2013.01); *B29L 2031/753* (2013.01); *B32B 2535/00* (2013.01); *Y10T 156/10* (2015.01)

(56) References Cited

U.S. PATENT DOCUMENTS

| | | | |
|---|---|---|---|
| 3,674,019 | A | 7/1972 | Grant |
| 4,043,345 | A | 8/1977 | Kramann et al. |
| 4,311,146 | A | 1/1982 | Wonder |
| 4,327,736 | A | 5/1982 | Inoue |
| 4,347,633 | A | 9/1982 | Gammons et al. |
| 4,483,030 | A | 11/1984 | Flick et al. |
| 4,555,242 | A | 11/1985 | Saudagar |
| 4,650,463 | A | 3/1987 | LeVeen et al. |
| 4,784,133 | A | 11/1988 | Mackin |
| 4,994,033 | A | 2/1991 | Shockey |
| 5,014,695 | A | 5/1991 | Benak et al. |
| 5,022,109 | A | 6/1991 | Pekar |
| 5,116,310 | A | 5/1992 | Seder et al. |
| 5,133,776 | A | 7/1992 | Crowder |
| 5,209,799 | A | 5/1993 | Vigil |
| 5,219,792 | A | 6/1993 | Kim et al. |
| 5,234,454 | A | 8/1993 | Bangs |
| 5,304,135 | A | 4/1994 | Shonk |
| 5,309,896 | A | 5/1994 | Moll et al. |
| 5,355,087 | A | 10/1994 | Claiborne et al. |
| 5,360,414 | A | 11/1994 | Yarger |
| 5,369,828 | A | 12/1994 | Graebe |
| 5,388,292 | A | 2/1995 | Stinson et al. |
| 5,433,252 | A | 7/1995 | Wolf et al. |
| 5,449,371 | A | 9/1995 | Pinchuk et al. |
| 5,451,232 | A | 9/1995 | Rhinehart et al. |
| 5,458,572 | A | 10/1995 | Campbell et al. |
| 5,512,051 | A | 4/1996 | Wang et al. |
| 5,527,280 | A | 6/1996 | Goelz |
| 5,545,122 | A | 8/1996 | Spruill |
| 5,545,220 | A | 8/1996 | Andrews et al. |
| 5,598,593 | A | 2/1997 | Wolfe |
| 5,679,423 | A | 10/1997 | Shah |
| 5,704,913 | A | 1/1998 | Abele et al. |
| 5,716,329 | A | 2/1998 | Dieter |
| 5,743,852 | A | 4/1998 | Johnson |
| 5,776,159 | A | 7/1998 | Young |
| 5,782,800 | A | 7/1998 | Yoon |
| 5,833,915 | A | 11/1998 | Shah |
| 5,843,116 | A | 12/1998 | Crocker et al. |
| 5,855,588 | A | 1/1999 | Young |
| 5,865,729 | A | 2/1999 | Meehan et al. |
| 5,868,705 | A | 2/1999 | Bagaoisan et al. |
| 5,868,776 | A | 2/1999 | Wright |
| 5,879,499 | A | 3/1999 | Corvi |
| 5,890,245 | A * | 4/1999 | Klearman et al. ............ 5/714 |
| 5,924,456 | A | 7/1999 | Simon |
| 5,935,115 | A | 8/1999 | Espina |
| 5,947,991 | A | 9/1999 | Cowan |
| 5,951,514 | A | 9/1999 | Sahota |
| 5,996,639 | A | 12/1999 | Gans et al. |
| 6,015,382 | A | 1/2000 | Zwart et al. |
| 6,022,313 | A | 2/2000 | Ginn et al. |
| 6,066,154 | A | 5/2000 | Reiley et al. |
| 6,102,929 | A | 8/2000 | Conway et al. |
| 6,110,142 | A | 8/2000 | Pinchuk et al. |
| 6,120,523 | A | 9/2000 | Crocker et al. |
| 6,156,053 | A | 12/2000 | Gandhi et al. |
| 6,217,548 | B1 | 4/2001 | Tsugita et al. |
| 6,249,708 | B1 | 6/2001 | Nelson et al. |
| 6,291,543 | B1 | 9/2001 | Shah |
| 6,312,462 | B1 | 11/2001 | McDermott et al. |
| 6,352,077 | B1 | 3/2002 | Shah |
| 6,371,910 | B1 | 4/2002 | Zwart et al. |
| 6,409,741 | B1 | 6/2002 | Crocker et al. |
| 6,460,541 | B1 | 10/2002 | Shah et al. |
| 6,478,029 | B1 | 11/2002 | Boyd et al. |
| 6,478,789 | B1 | 11/2002 | Spehalski et al. |
| 6,510,574 | B2 | 1/2003 | Sharrock et al. |
| 6,520,977 | B2 | 2/2003 | Piraka |
| 6,663,646 | B1 | 12/2003 | Shah |
| 6,712,832 | B2 | 3/2004 | Shah |
| 6,733,512 | B2 | 5/2004 | McGhan |
| 6,746,465 | B2 | 6/2004 | Diederich et al. |
| 6,805,662 | B2 | 10/2004 | Shah et al. |
| 6,827,710 | B1 | 12/2004 | Mooney et al. |
| 6,875,193 | B1 | 4/2005 | Weisel et al. |
| 6,939,339 | B1 | 9/2005 | Axexandersen et al. |
| 6,942,679 | B1 | 9/2005 | Terai |
| 6,981,980 | B2 | 1/2006 | Sampson et al. |
| 7,041,056 | B2 | 5/2006 | Deslauriers et al. |
| 7,112,186 | B2 | 9/2006 | Shah |
| 7,121,915 | B2 | 10/2006 | Banks et al. |
| 7,470,251 | B2 | 12/2008 | Shah |
| 7,666,205 | B2 | 2/2010 | Weikel et al. |
| 7,976,497 | B2 * | 7/2011 | Shah et al. ............ 604/103.06 |
| 2001/0011174 | A1 | 8/2001 | Reiley et al. |
| 2003/0028097 | A1 | 2/2003 | D'Amico et al. |
| 2003/0028211 | A1 | 2/2003 | Crocker et al. |
| 2003/0029182 | A1 * | 2/2003 | Augustine et al. .......... 62/259.3 |
| 2003/0088209 | A1 | 5/2003 | Chiu et al. |
| 2003/0105481 | A1 * | 6/2003 | Fogarty ............... A61M 1/1068 |
| | | | 606/192 |
| 2004/0064089 | A1 | 4/2004 | Kesten et al. |
| 2005/0015047 | A1 | 1/2005 | Shah |
| 2005/0222329 | A1 | 10/2005 | Shah |
| 2006/0212064 | A1 | 9/2006 | Shah |
| 2007/0010845 | A1 * | 1/2007 | Gong ............... A61B 17/8855 |
| | | | 606/192 |

(56) References Cited

U.S. PATENT DOCUMENTS

| | | |
|---|---|---|
| 2007/0212559 A1 | 9/2007 | Shah |
| 2007/0239110 A1 | 10/2007 | Shah |
| 2007/0299463 A1 | 12/2007 | Shah |
| 2008/0086083 A1 | 4/2008 | Towler |
| 2008/0172080 A1 | 7/2008 | Isham |
| 2008/0188802 A1 | 8/2008 | Shah |
| 2008/0262449 A1 | 10/2008 | Shah et al. |
| 2008/0262450 A1 | 10/2008 | Shah et al. |
| 2009/0082724 A1 | 3/2009 | Shah et al. |
| 2010/0137797 A2 | 6/2010 | Shah, T. et al. |
| 2011/0295202 A1 | 12/2011 | Shah et al. |

FOREIGN PATENT DOCUMENTS

| | | |
|---|---|---|
| JP | 51-101084 A | 9/1976 |
| JP | 6384565 A | 4/1988 |
| JP | 4129570 A | 4/1992 |
| JP | 10-127771 A | 5/1998 |
| WO | 9814123 A1 | 4/1998 |
| WO | 9920321 A2 | 4/1999 |

OTHER PUBLICATIONS

Civil Action No. 5:11-CV-0062-D, U.S. District Court for the Eastern District of North Carolina, Western Division; filed Nov. 21, 2011; pending litigation.

Civil Action No. 5:12-Cv-00102-D, U.S. District Court for the Eastern District of North Carolina, Western Division; filed Dec. 23, 2011; litigation proceedings consolidated with Civil Action No. 5:11-CV-0062-D by order on Jul. 2, 2012.

\* cited by examiner

MULTI-LAYER FILM WELDED ARTICULATED BALLOON

CROSS-REFERENCE TO RELATED APPLICATIONS

This application is a continuation under 35 U.S.C. §120 of U.S. patent application Ser. No. 13/154,229 filed Jun. 6, 2011 in the names of TILAK M. SHAH and CHRISTOPHER D. STROM for "Multi-Layer Film Welded Articulated Balloon," which is a continuation under 35 U.S.C. §120 of U.S. patent application Ser. No. 12/237,897 filed Sep. 25, 2008 in the names of TILAK M. SHAH and CHRISTOPHER D. STROM for "Multi-Layer Film Welded Articulated Balloon" and issued Jul. 12, 2011 as U.S. Pat. No. 7,976,497, which in turn claims the benefit of priority under 35 U.S.C. §119 of U.S. Provisional Patent Application No. 60/974,884 filed Sep. 25, 2007 in the names of TILAK M. SHAH and CHRISTOPHER D. STROM for "Multi-Layer Film Welded Articulated Balloon." The disclosures of each of the foregoing U.S. patent application Ser. No. 13/154,229, U.S. Pat. No. 7,976,497 and U.S. Provisional Patent Application No. 60/974,884 are hereby incorporated herein by reference, in their respective entireties for all purposes.

BACKGROUND OF THE INVENTION

Field of the Invention

The present invention relates to low pressure medical balloon articles and to the methodology for making the same, and in particular to a medical balloon useful for in vivo luminal medical procedures.

Description of the Prior Art

Various balloon articles are in use for cardiovascular and other medical procedures (such as percutaneous transluminal angioplasty, percutaneous transluminal nephrostomy, urethral dilatation, biliary duct dilatation, percutaneous transluminal renal angioplasty, and the like). Balloons may be utilized for such procedures, that are inflatable or otherwise capable of holding pressure. Pressure levels of balloons may be widely varied, depending on the specific application, and may for example be in a range of from 30-150 pounds per square inch (psi) for higher pressures and balloons and 1-10 psi for low pressure balloons.

Low pressure balloons are there which can hold a pressure on the order of 1-3 psi. Low pressure balloons are typically used for gastrointestinal applications. In other applications, balloons are employed in cardiovascular applications for blocking blood flow, or for removing/blocking a blood clot. In such applications, the balloon is typically bonded to the shaft of a catheter, and after inflation and use, the balloon is readily retracted to an original catheter sleeve shape.

An issue confronting the use of balloon articles for in vivo usage is the asymmetric character of the inflation.

There have been various attempts to shape the balloon so it can be articulated after inflation in vivo for its intended use. For example, in angioplasty applications, clots found in arteries should be held against the artery walls until treated or removed. In prostate treatments it is often desirable to space the prostate from the rectum while treating the same with radiation.

Usually, to achieve the desired inflated shape in low pressure balloons, the balloon material, often latex, is pre-stretched so as to achieve the desired final shape or the balloon has discrete portions which are overinflated so as to assume a desired shape after insertion and inflation. Another tactic employed is to precure particular selected balloon material so that when inflated, the balloon will assume the precured shape, or to form the balloon with a wall thickness which may vary at different locations in the balloon so as to expand at different rates to achieve different shaped portions in the balloon.

While the resultant balloon would be operational for its intended purpose, each requires an involved fabrication methodology.

SUMMARY OF THE INVENTION

The present invention relates to balloon articles useful in various medical procedures.

In one aspect, the present invention provides a method of fabrication of a medical balloon which uses at least two layers of a thermoplastic film sealed at their edges or periphery and heat sealed at one or more locations inside the area enclosed by the sealed edge at preselected locations, which enables the balloon to articulate to a desired shape upon inflation, with the specific shape being dependent on the particular medical application. The layers may have a different thickness or modulus of elasticity or any combination thereof or the same thickness and modulus, and different dimensioned channels formed by the heat sealed locations to articulate to a desired shape.

In a specific aspect, the invention relates to a method for the fabrication of an articulated medical balloon device comprising the steps of:

(a) providing at least two film layers having opposed edges;

(b) sealing said opposed edges to form a compartment adapted to receive fluid to expand said film layers relative to each other;

(c) providing an opening in said fluid compartment that is adapted to receive a lumen; and (d) forming a subcompartment between the sealed edges of said compartment of a predetermined shape and dimension by sealing at least one of said layers to another, intermediate said opposed edges.

In a further aspect, the invention relates to a medical balloon device, comprising:

at least one film layer having an edge secured to a second film layer to form a fluid compartment therebetween, and portions of said film layers between said edges being secured intermediate said edges to form a plurality of subcompartments, and said fluid compartment being provided with an opening to receive a lumen.

Additional aspects, features and embodiments will be more fully apparent from the ensuing disclosure and appended claims.

DETAILED DESCRIPTION OF THE PREFERRED EMBODIMENTS

Figure 1:
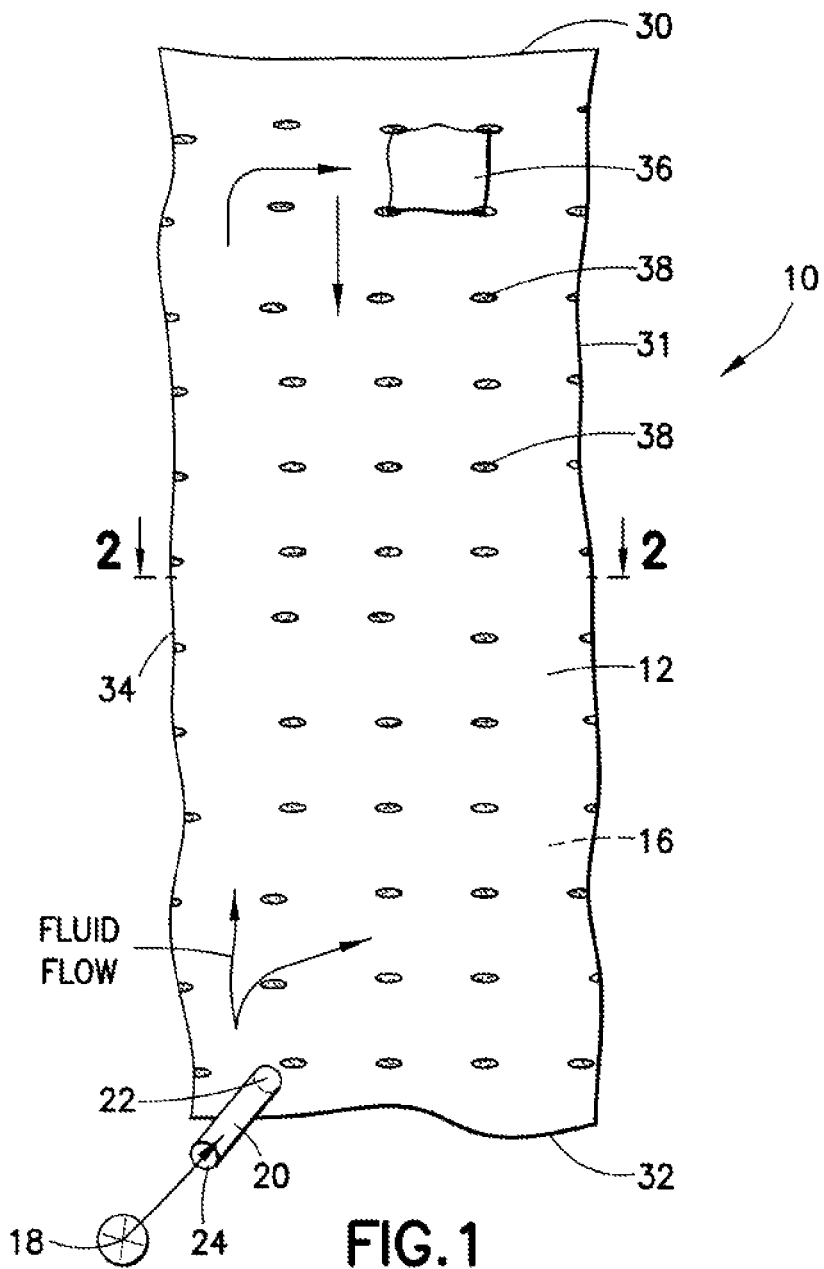
FIG. 1 is a top plan view of one embodiment of the balloon of the present invention.
Figure 2:
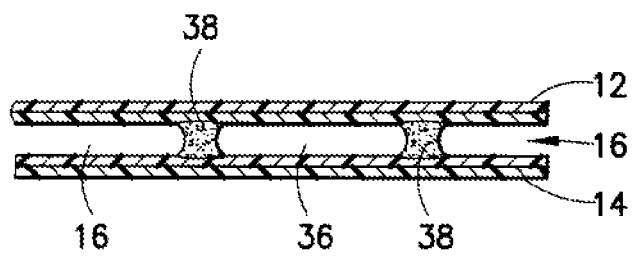
FIG. 2 is a cross-sectional view of the balloon of FIG. 1 taken substantially along the plane indicated by the line 2-2 of FIG. 1.

Referring now to the drawings in detail, wherein like numerals indicate like elements throughout the several views, each of the inflatable balloon structures of the present invention, e.g., the balloon structure 10 of FIG. 1, comprises a multilayer arrangement of film layers 12, 14 or more, that includes an inflatable compartment 16 defining an enclosed interior volume and an anti-reflux valve 18 positioned in a lumen or fluid passage 20 whose distal end 22 is sealingly connected to the interior volume of compartment 16. An inflation bulb is connected to the proximal end 24 of lumen 20 upstream from the anti-reflux valve 18. The valve 18 may be a one-way check valve or a rotatable stem in a housing having an opening adapted to be rotated into alignment with the bore of the lumen 20.

Oppositely facing film layers 12, 14 are bonded to one another along their edges 30, 31, 32 and 34 to form the inflatable compartment 16 and the compartment 16 is divided into subcompartments 36 by tack or spot welds 38 so that the subcompartments 36 are virtually square-shaped in plan so that upon inflation, the balloon compartment 16 will resemble a tufted cushion with the tack or spot welds 38 forming raised square-shaped subcompartments. This device can be used to separate two organs in the body in vivo and support the same in spaced relation.

The inflatable balloon compartment and subcompartments can be readily formed by heat-sealing or other joining techniques commonly known and used in the art for forming structural articles from thermoplastic film materials in the form of web or sheet stock. For example, RF welding, heat impulse welding, solvent welding, adhesive bonding and the like can be employed.

Figure 3:
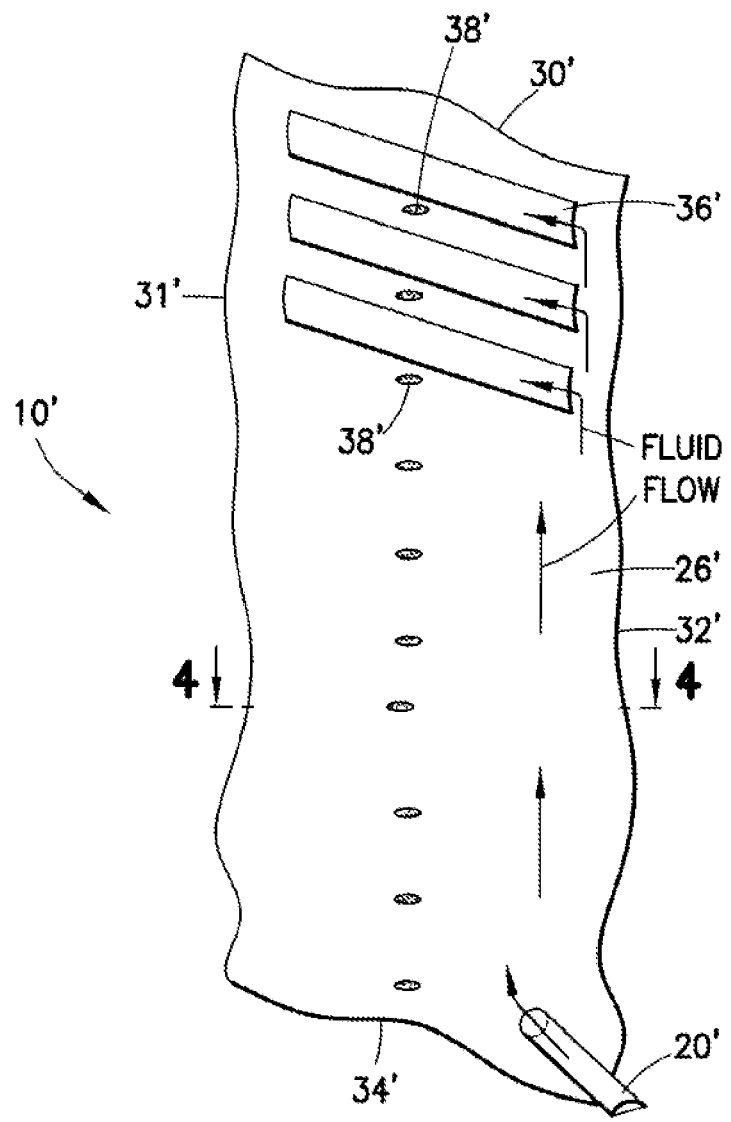
FIG. 3 is a top plan view of a second embodiment of the balloon of the present invention.
Figure 4:
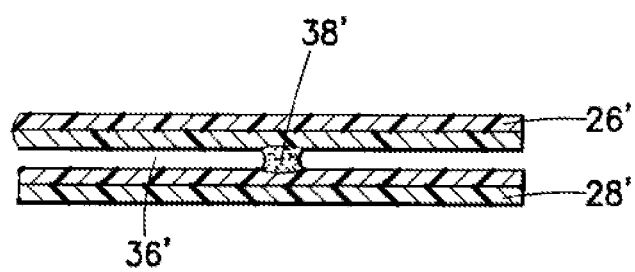
FIG. 4 is a cross-sectional view of the balloon of FIG. 3 taken substantially along the plane indicated by the line 4-4 of FIG. 3.
Figure 5:
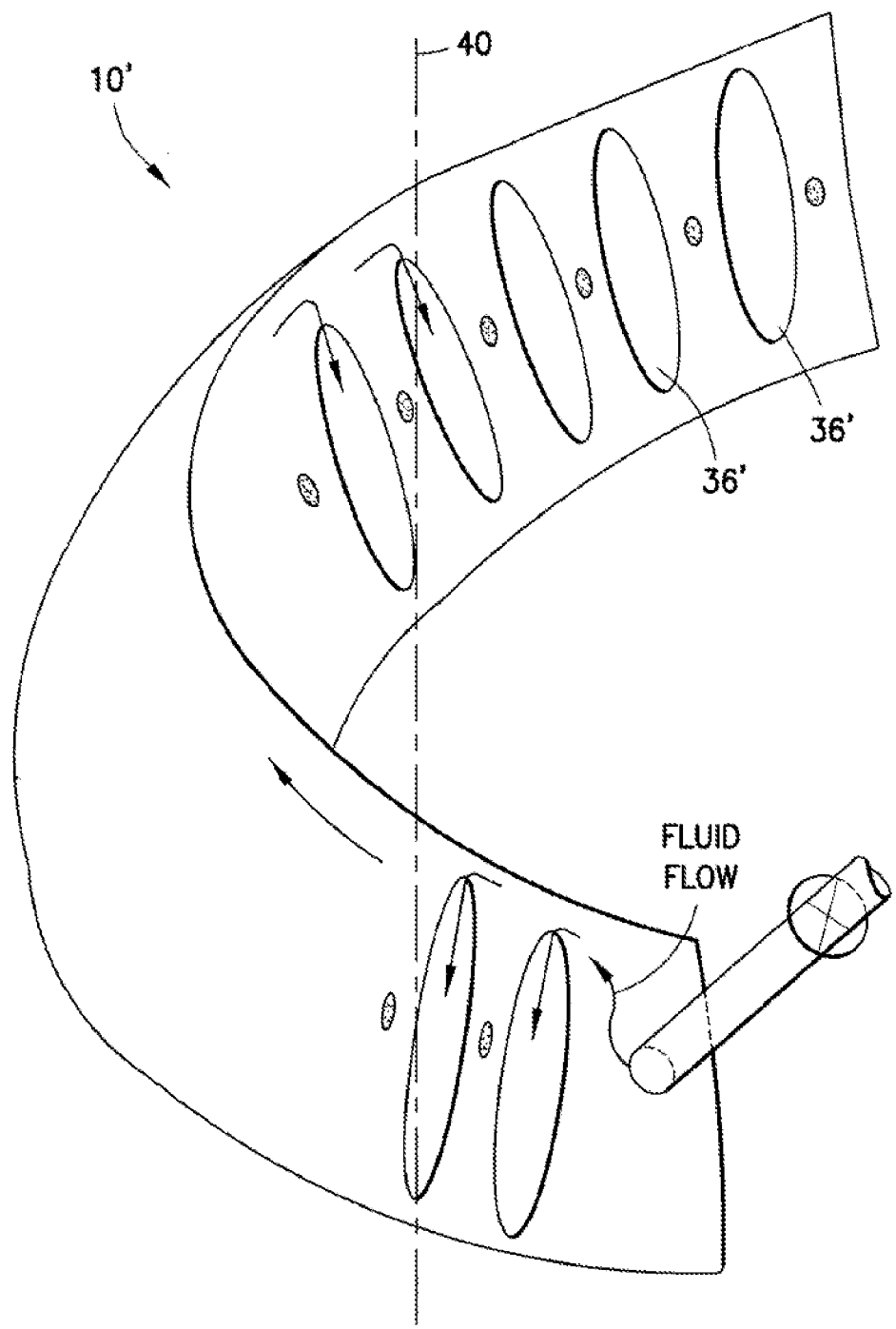
FIG. 5 is a perspective view of the articulated balloon of FIG. 3 after inflation.

Referring to the embodiment of the invention illustrated in FIGS. 3 to 5, inclusive, the film layers 26' and 28' may be bonded to each other in the shape of a parallelogram, with subcompartments 36' extending in spaced relation to each other, but parallel to the side edges 30' and 34' and at an angle to the opposite edges 31' and 32' by tack or spot welds 38'. As shown in FIG. 5, upon inflation, the fluid force introduced into the subcompartments 36' will cause the balloon device 10' to curl into a spiral about a longitudinal axis 40.

Figure 6:
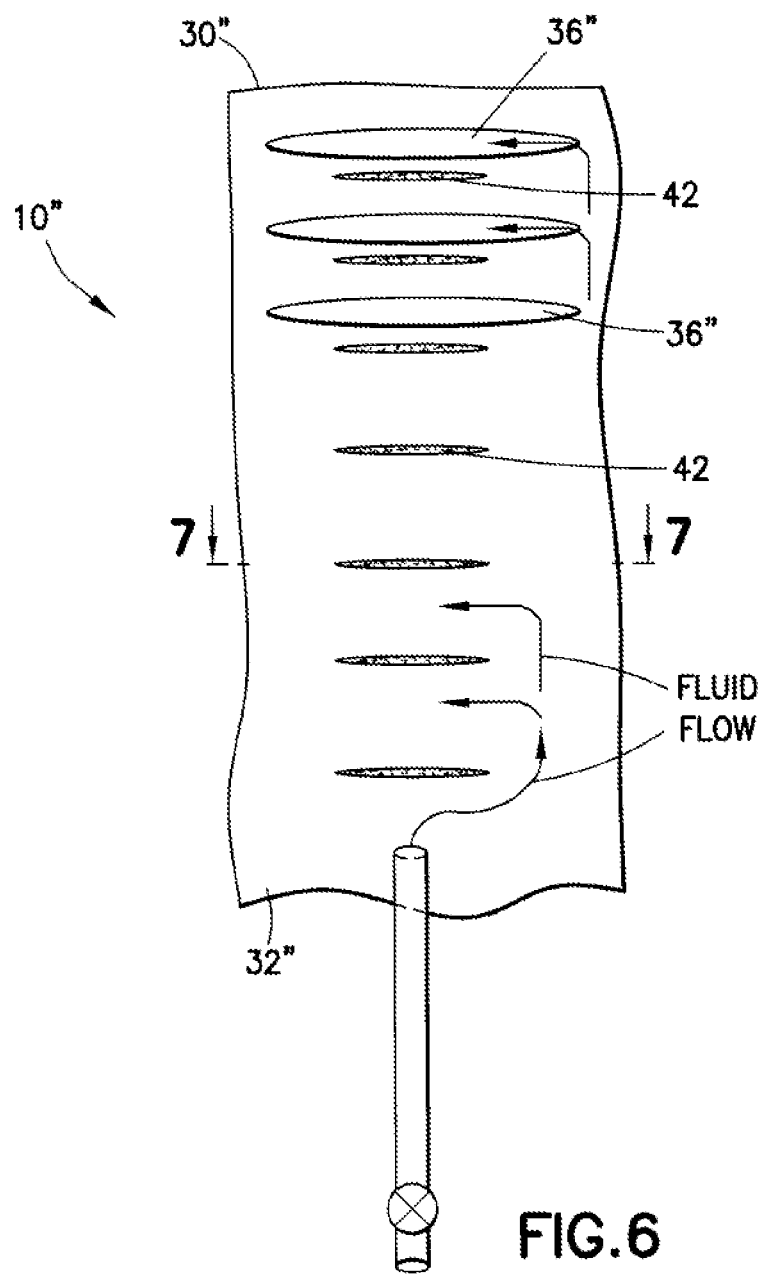
FIG. 6 is a top plan view of yet another embodiment of the balloon of the present invention.
Figure 7:
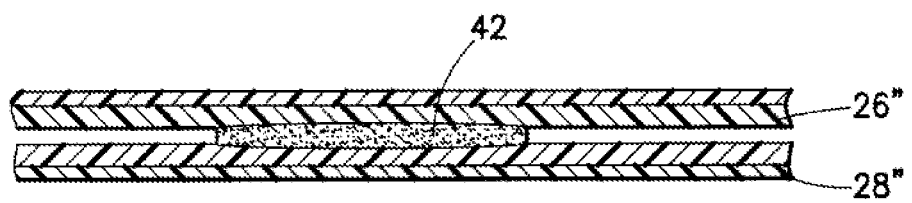
FIG. 7 is a cross-sectional view of the balloon of FIG. 6 taken substantially along the plane indicated by line 7-7 of FIG. 6.

Referring to FIGS. 6 and 7, the balloon device 10" can be formed with rectangular subcompartments 36" utilizing line welds 42, parallel to edges 30" and 32".

Figure 8:
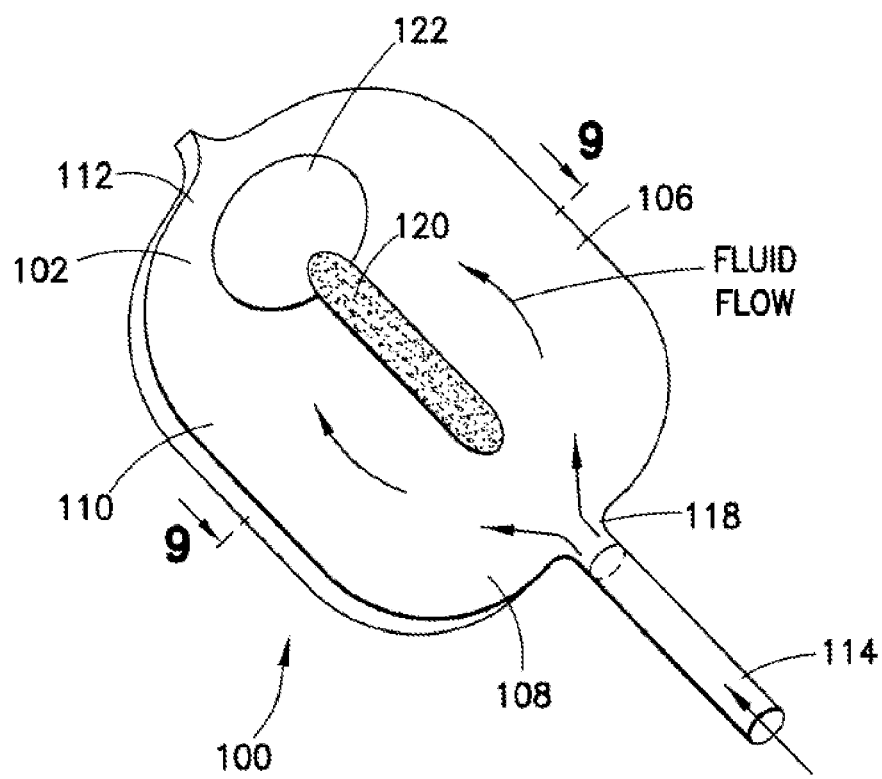
FIG. 8 is a perspective view of still another embodiment of an articulated balloon according to the present invention.
Figure 9:
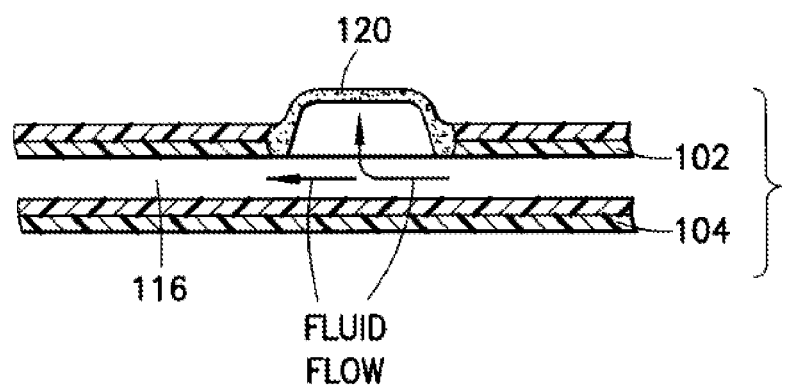
FIG. 9 is a cross-sectional view of the balloon of FIG. 8 taken substantially along the plane indicated by line 9-9 of FIG. 8.

As shown in the embodiment illustrated in FIGS. 8 and 9, the balloon device 100 has thermoplastic film layers 102 and 104 having different properties joined along their edges 106, 108, 110, and 112. For example, the materials can have a different modulus of elasticity, meaning that they will stretch under pressure at different rates to form a particular arcuate or curved shape. In this embodiment, the lumen 114 can extend into the interior of the compartment 116 formed by the film layers 102 and 104 and sealed to the balloon at neck 118.

Additionally, a third layer or strip of film 120 can be added or joined to the top layer 102 to increase its thickness. This will cause the sides 108, 112 to be drawn inwardly relative to the lumen axis, upon inflation, while the distal or forward portion of the compartment 122 will bulge upwardly. Such a device is useful in prostate surgery to support the prostate in spaced relation to other organs.

It will therefore be appreciated that the medical balloon device of the invention may be widely varied in construction and features. In one embodiment, the balloon device includes at least one neck member in a sealing area of the device. The device in a further embodiment comprises at least one area outside of the secured edges forming an inflation port.

While the invention has been illustratively shown and described with respective to particular embodiments, it will be appreciated that the application is not thus limited, but rather extends to and encompasses other variations, modifications and additional embodiments as will be apparent to those of ordinary skill in the art, based on the disclosure herein. Accordingly, the invention is intended to be broadly construed with respect to the ensuing claims, as encompassing all such additional variations, modifications and alternative embodiments.

What is claimed is:

1. A multi-layer film heat welded medical balloon device comprising a multiplicity of layers of thermoplastic film including at least two thermoplastic film layers heat welded at peripheral edges to form a compartment adapted to receive fluid to expand said film layers relative to each other, and heat welded at one or more locations inside an area enclosed by the heat welded peripheral edges so as to enable the balloon device to articulate to a desired shape upon inflation, with a third thermoplastic film layer of said multiplicity of layers arranged so that a distal portion of the balloon device will bulge upwardly to form said desired shape upon inflation, and at least one of the layers heat welded to another of said layers, intermediate said peripheral edges, to form subcompartments in fluid communication with one another in said compartment that are configured to enable the device to articulate to said desired shape, wherein all layers are heat welded to one another at peripheral edges thereof, wherein all heat welded locations of said medical balloon device comprise heat weld regions on the thermoplastic film layers joining the thermoplastic film layers at said locations to one another.

2. The medical balloon device of claim 1, comprising a fluid passage member sealed at a proximal neck of the balloon device for inflation of the balloon device.

3. The medical balloon device of claim 1, wherein said desired shape is effective to support a prostate in spaced relation to other organs during prostate surgery.

4. The medical balloon device of claim 1, wherein said multiplicity of layers comprises layer(s) of different thickness.

5. The medical balloon device claim 1, wherein said multiplicity of layers comprises layer(s) of different modulus of elasticity.

6. A multi-layer film heat welded medical balloon device, comprising a multiplicity of layers of thermoplastic film including first and second thermoplastic film layers heat welded to one another to form a first inflatable compartment, and a third thermoplastic film layer heat welded to the second thermoplastic film layer to form a second inflatable compartment, wherein the first and second inflatable compartments are in fluid communication with one another in an inflatable interior volume sealed by heat welded thermoplastic film edges, and arranged so that upon inflation of the medical balloon device, a distal portion of the balloon device will bulge upwardly, wherein all layers are heat welded to one another at peripheral edges thereof, and wherein at least one of the layers is heat welded to another of said layers, intermediate said peripheral edges, to enable the distal portion of the balloon device to bulge upwardly, wherein all heat welded locations of said medical balloon device comprise heat weld regions on the thermoplastic film layers joining the thermoplastic film layers at said locations to one another.

7. The medical balloon device of claim 6, comprising a fluid passage member communicating with said interior volume and sealed at a proximal neck of the balloon device.

8. The medical balloon device of claim 6, wherein the balloon device upon inflation and upward bulging of the distal portion thereof is effective to support a prostate in spaced relation to other organs during prostate surgery.

9. The medical balloon device of claim 6, wherein said multiplicity of layers comprises layer(s) of different thickness.

10. The medical balloon device claim 6, wherein said multiplicity of layers comprises layer(s) of different modulus of elasticity.

* * * * *